United States Patent [19]

Northeved et al.

[11] Patent Number: 4,844,081
[45] Date of Patent: Jul. 4, 1989

[54] DEVICE FOR DISINTEGRATING KIDNEY STONES BY MEANS OF SHOCK WAVES

[75] Inventors: Allan Northeved, Farum; Gert Toftkjaer, Naerum, both of Denmark

[73] Assignee: Non-Invasive Therapeutic Techniques A/S, Virum, Denmark

[21] Appl. No.: 89,502

[22] Filed: Aug. 26, 1987

[51] Int. Cl.$^4$ .......................... A61B 8/00; A61B 17/22
[52] U.S. Cl. .............................. 128/660.03; 128/24 A; 128/328
[58] Field of Search ..................... 128/24 A, 328, 660, 128/660.03

[56] References Cited

U.S. PATENT DOCUMENTS

| | | | |
|---|---|---|---|
| 4,541,434 | 9/1985 | Okada | 128/660 |
| 4,610,249 | 9/1986 | Makorski et al. | 128/328 |
| 4,620,545 | 11/1986 | Shene et al. | 128/328 |
| 4,669,483 | 6/1987 | Hepp et al. | 128/328 |

FOREIGN PATENT DOCUMENTS

| | | | |
|---|---|---|---|
| 3328068 | 2/1985 | Fed. Rep. of Germany | 128/328 |
| 3444421 | 6/1986 | Fed. Rep. of Germany | 128/328 |
| 3617032 | 1/1987 | Fed. Rep. of Germany | 128/328 |
| 3543867 | 6/1987 | Fed. Rep. of Germany | 128/328 |

Primary Examiner—Ruth S. Smith
Attorney, Agent, or Firm—Ladas & Parry

[57] ABSTRACT

A device for disintegrating kidney stones or gallstones by means of a focusing chamber being part of a rotation ellipsoid and comprising in one focal point a spark gap producing shock waves. Means fixing the device to the skin of the patient are provided in connection with the focusing chamber. A movable rubber sleeve or bellows may be provided in connection with the fixing means, said sleeve or bellows being glued onto the skin of the patient. As an alternative circumferential suction chambers may be provided along the rim of the sleeve, or the entire device may be shaped as a suction cup. An ultrasonic transducer is situated within the focusing chamber, said ultrasonic transducer optionally being situated on a cone-shaped body in turn situated on a pivotable bar within the focusing chamber. In this manner it is possible to localize a stone by means of an ultrasonic scanner without the ultrasonic transducer in question being damaged by shock waves.

5 Claims, 5 Drawing Sheets

DEVICE FOR DISINTEGRATING KIDNEY STONES BY MEANS OF SHOCK WAVES

FIELD OF THE INVENTION

The invention relates to a device for disintegrating stones by means of a focusing chamber being part of an ellipsoid, preferably a rotation ellipsoid, and comprising in one focal point a spark gap producing shock waves.

BACKGROUND ART

In connection with one of the known devices the patient is situated in a tub containing water transmitting the shock waves.

According to a second device the tub is avoided by the focusing chamber being filled with water and covered by a thin membrane. This membrane abuts the skin of the patient, see, for example, DE-OS No. 3,146,626.

SUMMARY OF THE INVENTION

According to the invention the above membrane has been avoided by means in connection with the rim of the focusing chamber, said means fixing the device to the skin of the patient.

According to a particularly advantageous embodiment a movable sleeve, such as a rubber sleeve, is provided in connection with the fixing means. The sleeve is optionally glued onto the skin of the patient. As an alternative circumferential suction chambers or suction cups may be provided along the rim of the sleeve, or the entire device may be shaped as a suction cup.

According to an alternative embodiment a telescopic tube is provided in connection with the fixing means, said tube being able to tightly abut the skin of the patient as the intersection can be shaped in different ways. Such a device is optionally built in a patient table in such a manner that the weight of the patient presses said patient towards the device whereby the rim of the telescopic tube tightly abuts the skin.

BRIEF DESCRIPTION OF DRAWING

The invention will be described below with reference to the accompanying drawings, in which.

DESCRIPTION OF PREFERRED EMBODIMENTS

Figure 1:
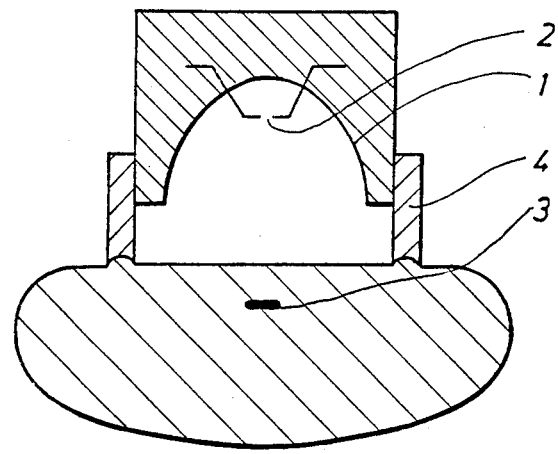
FIG. 1 illustrates a device disintegrating kidney stones by means of acoustic shock waves.
Figure 2:
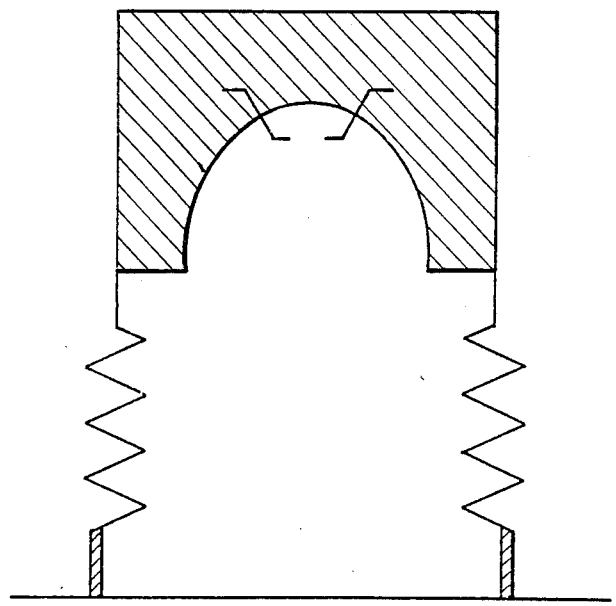
FIG. 2 illustrates the kidney stone disintegrator of FIG. 1, a movable sleeve being provided in connection with the ellipsoidal reflector.
Figure 3:
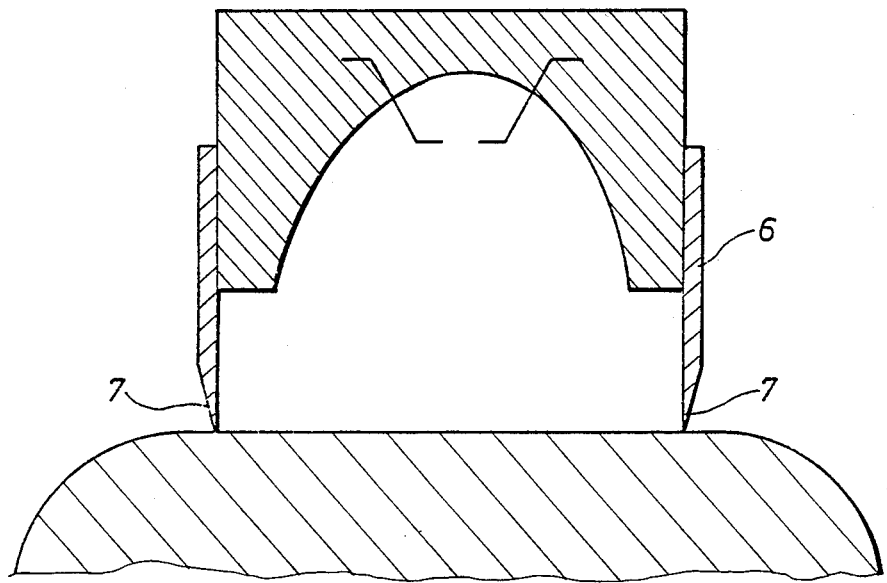
FIG. 3 illustrates a second embodiment of the kidney stone disintegrator, whereby a telescopic tube tightly abutting the skin of the patient is provided in connection with the fixing means.
Figure 4:
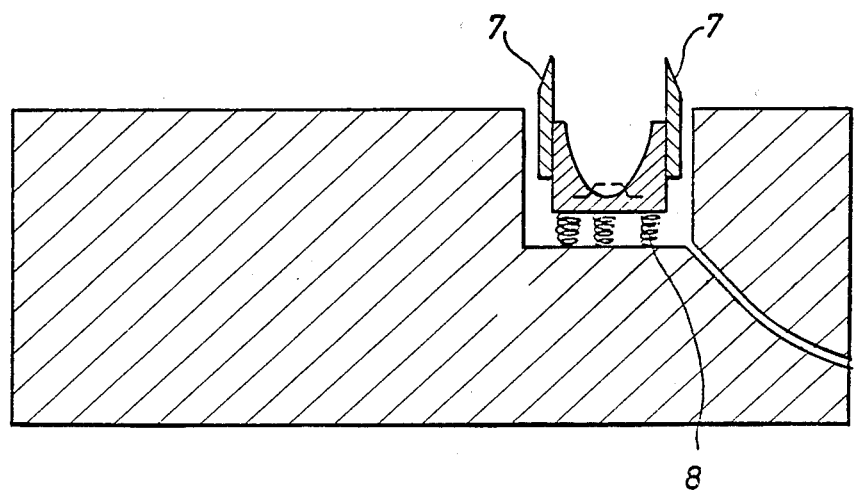
FIG. 4 illustrates the kidney stone disintegrator of FIG. 3 situated in a patient table.

The device of FIG. 1 for disintegrating kidney stones comprises a focusing chamber 1 being part of an ellipsoid. A spark gap 2 producing shock waves is situated in one focal point of the ellipsoid, said shock waves being reflected by the ellipsoid and focussed in the second focal point. The kidney stone 3 has been localized in advance by means of an ultrasonic scanner producing a sectional view of the patient, said sectional view appearing on an oscillo scope and simultaneously showing the focal points of the ellipsoid and a line of sight passing through said focal points. An example of such an ultrasonic scanner is described in Danish Pat. Application No. 2084/75. Subsequently the ellipsoid is oriented in such a manner that the outer focal point is situated in the center of a kidney stone 3. The spark gap 2 is of a conventional type and for instance of the type described in DE-OS No. 3,146,627. The voltage fed is of the magnitude 20,000 V. The reflector has been filled with a liquid, such as water, providing the best possible acoustic transmission. The reflector 1 is associated with a rubber sleeve or bellows 4 directly abutting the skin of the patient. The rubber sleeve or bellows 4 may for instance be glued onto the skin of the patient. Such a bellows 4, see, for example, FIG. 2, is advantageous by facilitating the orientation of the ellipsoidal reflector 1. Circumferential fixing means in the form of vacuum chambers may be provided also, said chambers optionally being divided in such a manner that a possible leak does not influence the entire sleeve. As an alternative, a telescopic tube 6, see, for example, FIG. 3, may be provided, said tube ending in one or more rims 7 tightly abutting the skin. Such a reflector can by its weight be pressed against the skin of the patient and may be provided in a patient table, cf. FIG. 4, in such a manner that due to his own weight the patient is pressed against the device, the rim 7 of the telescopic tube tightly abutting the skin of the patient. The device is pressed upwards toward the skin of the patient by means of springs 8 situated therebelow. This device possesses the particular advantage that the tightness along the rim is not too critical. An outlet is optionally provided for the amount of liquid possibly leaking along the rim of the reflector or the telescopic tube. As an alternative the device can be situated above the patient and pressed downwards against the skin of the patient by a weight of a predetermined size. The device can also be secured to the patient by means of circumferential tapes.

Figure 5:
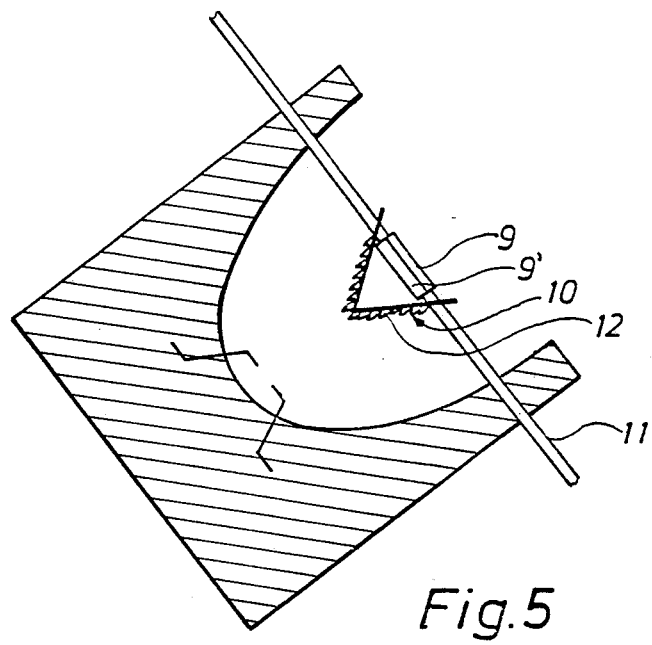
FIG. 5 illustrates a kidney stone disintegrator comprising an ultrasonic transducer localizing kidney stones.

Referring to FIG. 5, the ultrasonic transducer 9 can for instance be situated in a cone 10 secured to a pivotable bar 11 in the reflector. The outside of the cone 10 is coated with a shock wave-absorbing silicon rubber 12 having a corrugated surface. A layer of shock wave-reflecting material is situated below the above coating. The cone 10 is filled with air insulating against the transmission of shock waves. The crystal 9 is mounted on a base 9' absorbing rearward radiation from the crystal. This base 9' is according to the invention also used for absorbing the shock waves optionally reaching said base.

Figure 6:
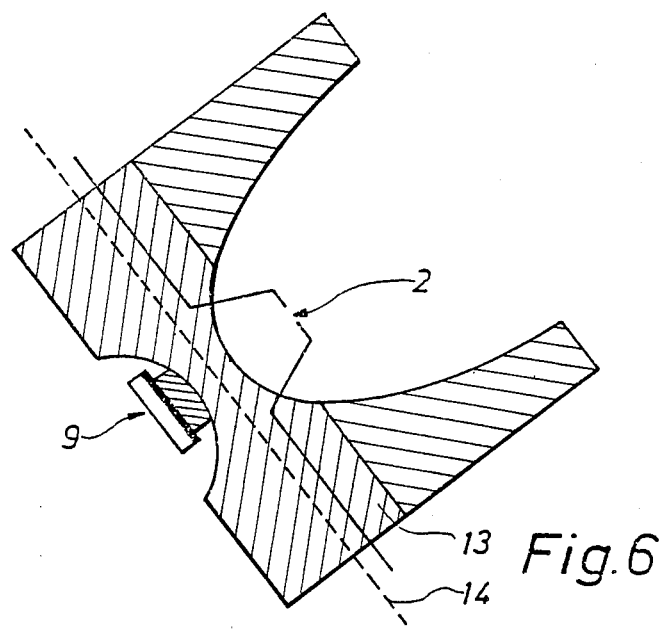
FIG. 6 illustrates a reflector with a pivotable lower portion allowing alternate use of the ultrasonic transducer for localizing the stone and the spark gap for producing shock waves.

According to an alternative embodiment the lower portion of the reflector is pivotable, a piezoelectric crystal 9 being situated on one side and a spark gap 2 being situated on the opposite side of said pivotable portion, see, for example, FIG. 6. The electrodes do not always stand a full shock wave treatment, and it is therefore a great advantage that the lower portion of the device is pivotable in such a manner that a replacement can be performed during a treatment. Both the spark gap and the transducer are fed with current through the pivotable portion of the reflector. As an alternative the transducer can be situated on a particular handle inserted from the side and being flush with the ellipsoid when retracted. As an alternative the scanning is performed by means of an oscillating mirror situated within the ellipsoid. The transducer is connected to an oscilloscope via known circuits, see, for example, for instance Danish Pat. Application No. 2084/75 showing a sectional view through the patient.

The ellipsoid is optionally of an elliptic cross section whereby the focal points are slightly blurred.

In order to improve the securing of the reflector to the skin it is possible to suck out amounts of air, if any, from the chamber filled with liquid. The suction is to be stopped when a sensor in the suction channel becomes wet.

According to the invention it has thus been demonstrated how to localize a kidney stone by means of an ultrasonic transducer without the ultrasonic crystal in question being damaged by shock waves.

According to a particular embodiment the reflector is set by means of a servo-system comprising a suitable number of servomotors (not shown). The desired setting of the outer focal point can either be inserted via a panel or by means of a joy-stick because it is possible to observe the setting on the screen. In most cases it is sufficient to employ three servomotors for setting the X, Y, and Z coordinates of the outer focal point relative to the kidney stone. The setting is optionally automatized by a computer initially computing the position of the kidney stone on the basis of an ultrasonic picture, and subsequently computing how the servosystem is to be set. Therefore the apparatus need not be handled by highly skilled persons but can be dealt with by less educated persons. The computer can also provide an estimate of the size of the stones upon a predetermined number of shock waves. As a result it is possible to estimate the number of further shock waves necessary for disintegrating the stone at the same time as the efficiency of the treatment is evaluated. In the case of several stones the computer alters automatically the setting upon a predetermined number of shock waves. The position of the stone alters at breathing. It is, however, possible by processing the computer picture to ensure that the shock wave is always focused in the stone either by said shock wave being omitted when the typical stone echo does not pass the second focal point of the ellipsoid or by the computer-controlled servomotors continuously keeping the focusing point on the stone.

Figure 7:
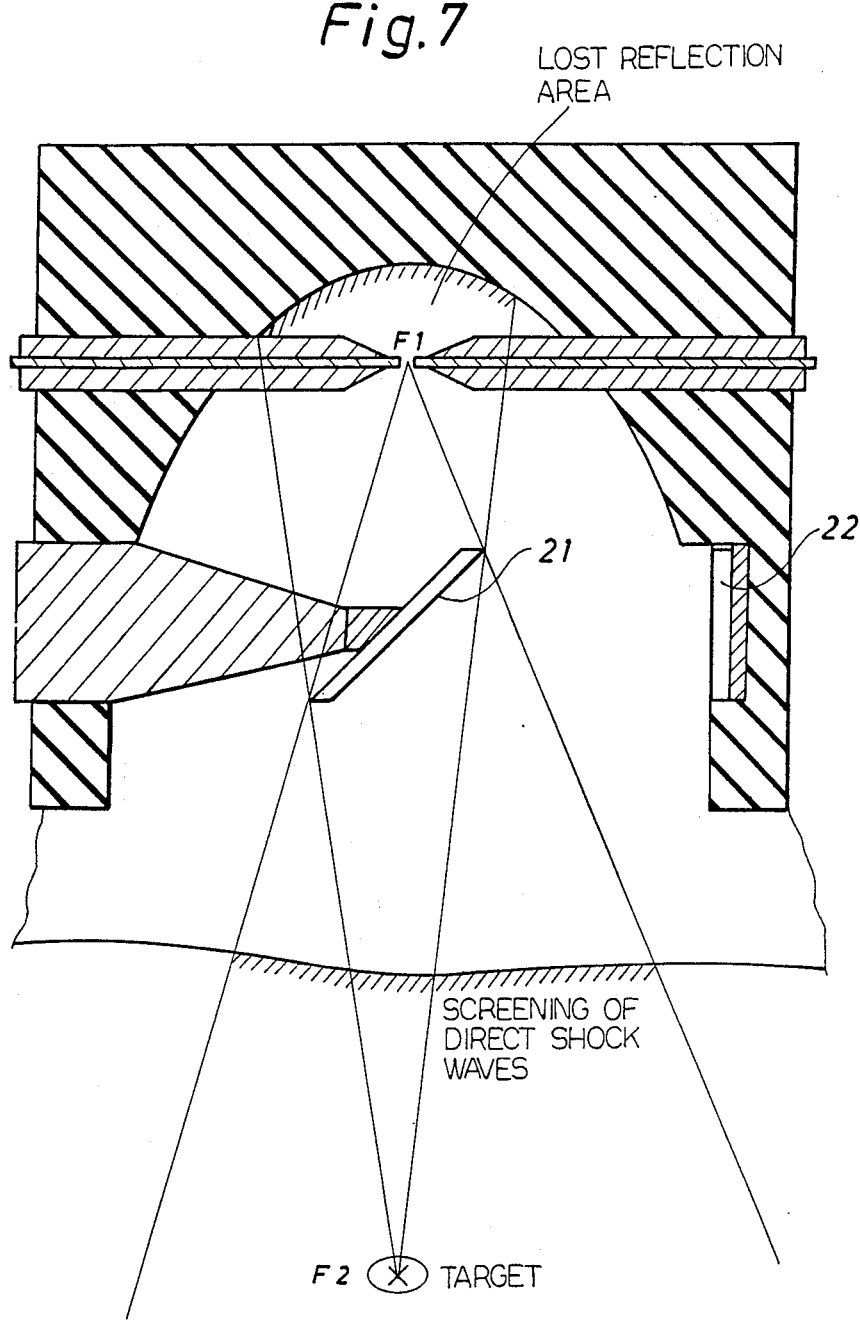
FIG. 7 illustrates a kidney stone disintegrator comprising a scanning mirror for localizing kidney stones.

According to an alternative embodiment, see, for example, FIG. 7, a pivotable mirror 21 is situated in the focusing chamber and an ultrasonic transducer 22 is fixed in the side of the concave mirror. The mirror 21 deflects the ultrasonic waves of the ultrasonic transducer 22 and can thereby during rotation perform the necessary scanning. An additional advantage of the scanning mirror is that it can also be used as a shield for direct shock waves in such a manner that the anaesthetization can apparently be reduced. Then the mirror 21 need only be shaped so as to provide a substantially symmetric shielding towards the direct shock waves. The mirror is preferably elliptic. Measures have, of course, been taken so as to ensure that the ultrasonic crystal is not damaged by the shock waves, e.g. by said ultrasonic crystal being situated in a pipe lined with a sound-absorbing material. However, the mirror 21 shields also against some of the shock waves used for kidney stone disintegration. It turned out that the reduction of the useful shock wave effect with approximation is proportional to the lost reflection area, see, for example, FIG. 7. In this manner it is possible to optimalize the angular position of the mirror during a kidney disintegration in such a manner that for instance the best possible ratio of useful to useless shock wave effect is obtained. The pivotable mirror can also be provided with an extra shielding plate pivotable relative to the mirror in such a manner that the shielded area is increased.

The apparatus may also be used for disintegrating gallstones.

We claim:

1. A device for disintegrating stones comprising:
   an ellipsoid focusing chamber;
   a spark gap located at one focal point of said ellipsoid and coupled to a source of voltage pulses for producing shock waves in said chamber for coupling to a stone;
   ultrasonic scanning means mounted within said chamber for localizing said stone, said scanning means comprising an ultrasonic transducer mounted in a side wall of said chamber and a rotatable reflecting mirror mounted inside said chamber.

2. A device according to claim 1, wherein the rotatable mirror is elliptic.

3. A device for disintegrating stones comprising:
   an ellipsoid focusing chamber;
   a spark gap located at one focal point at said ellipsoid and coupled to a source of voltage pulses for producing shock waves in said chamber for coupling to a stone;
   ultrasonic scanning means mounted within said chamber for localizing said stone, said scanning means comprising an ultrasonic crystal transducer fixedly mounted in a side wall of said chamber in a pipe lined with sound absorbing material and a rotatable reflecting mirror mounted inside said focusing chamber.

4. A device according to claim 3, wherein said rotatable mirror is shaped so as to provide substantially symmetric shielding of said crystal from direct shock waves.

5. A device according to claim 4, wherein said mirror is elliptic.

* * * * *